(12) United States Patent
Mahajan et al.

(10) Patent No.: US 9,764,144 B2
(45) Date of Patent: Sep. 19, 2017

(54) IMPLANTED LEAD ANALYSIS SYSTEM AND METHOD

(71) Applicant: Cardiac Pacemakers, Inc., St. Paul, MN (US)

(72) Inventors: Deepa Mahajan, Roseville, MN (US); David L. Perschbacher, Coon Rapids, MN (US); Arjun D. Sharma, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 66 days.

(21) Appl. No.: 14/811,901

(22) Filed: Jul. 29, 2015

(65) Prior Publication Data
US 2016/0030752 A1 Feb. 4, 2016

Related U.S. Application Data

(60) Provisional application No. 62/030,388, filed on Jul. 29, 2014.

(51) Int. Cl.
*A61B 5/0402* (2006.01)
*A61N 1/37* (2006.01)
(Continued)

(52) U.S. Cl.
CPC .............. *A61N 1/37* (2013.01); *A61B 5/0424* (2013.01); *A61N 1/056* (2013.01); *A61N 1/08* (2013.01); *A61N 2001/083* (2013.01)

(58) Field of Classification Search
CPC .... A61N 1/37; A61N 1/056; A61N 2001/083; A61N 1/08; A61B 5/0424
(Continued)

(56) References Cited

U.S. PATENT DOCUMENTS

| 5,814,088 A | 9/1998 | Paul et al. |
|---|---|---|
| 6,721,600 B2 | 4/2004 | Jorgenson et al. |

(Continued)

FOREIGN PATENT DOCUMENTS

WO 2016019048 2/2016

OTHER PUBLICATIONS

"International Search Report and Written Opinion," for PCT/US2015/042711 mailed Oct. 19, 2015 (12 pages).
(Continued)

*Primary Examiner* — Michael Carey
(74) *Attorney, Agent, or Firm* — Pauly, DeVries Smith & Deffner LLC

(57) ABSTRACT

Implanted medical device data is received, where the data was sensed by a first lead portion and a sensor over a time period. The number of detected noise events sensed by the first lead portion is counted based on applying first noise detection criteria to the data sensed by the first lead portion. The number of detected noise events over the sensor is counted based on applying second noise detection criteria to the data sensed by the sensor. The mean number of detected noise events is calculated for the first lead portion and sensor based on the number of noise events sensed by the first lead portion and the number of noise events sensed by the sensor. Potential lead failure in the first lead is recorded if the number of detected noise events over the first lead is greater than the mean number of noise events by at least 5%.

20 Claims, 11 Drawing Sheets

(51) Int. Cl.
*A61N 1/05* (2006.01)
*A61N 1/08* (2006.01)
*A61B 5/0424* (2006.01)

(58) Field of Classification Search
USPC .............................. 607/27, 5, 9, 28; 600/508
See application file for complete search history.

(56) References Cited

U.S. PATENT DOCUMENTS

| | | |
|---|---|---|
| 7,047,083 B2 | 5/2006 | Gunderson et al. |
| 7,289,851 B2 | 10/2007 | Gunderson et al. |
| 7,647,185 B2 | 1/2010 | Tarassenko et al. |
| 7,894,886 B2 | 2/2011 | Ghanem et al. |
| 7,974,690 B2 | 7/2011 | Kracker |
| 7,991,472 B2 | 8/2011 | Levine et al. |
| 7,991,492 B1 | 8/2011 | Namanny et al. |
| 8,099,166 B2 | 1/2012 | Schüller et al. |
| 8,249,709 B2 | 8/2012 | Davenport et al. |
| 8,260,419 B2 | 9/2012 | Gunderson |
| 8,483,813 B2 | 7/2013 | Zhang et al. |
| 8,626,293 B2 | 1/2014 | Bornzin et al. |
| 9,440,088 B2 | 9/2016 | Perschbacher et al. |
| 2003/0204215 A1 | 10/2003 | Gunderson et al. |
| 2008/0161870 A1* | 7/2008 | Gunderson ......... A61N 1/3702 607/5 |
| 2010/0312131 A1* | 12/2010 | Naware ............... A61B 5/0402 600/518 |
| 2011/0106191 A1* | 5/2011 | Bennett .................... A61N 1/37 607/5 |
| 2012/0158089 A1* | 6/2012 | Bocek ...................... A61N 1/37 607/28 |
| 2012/0203123 A1* | 8/2012 | Mahajan ............... A61B 5/024 600/509 |
| 2014/0163629 A1 | 6/2014 | Perschbacher et al. |

OTHER PUBLICATIONS

"International Preliminary Report on Patentability," for PCT Application No. PCT/US2015/042711 mailed Feb. 9, 2017 (10 pages).

* cited by examiner

IMPLANTED LEAD ANALYSIS SYSTEM AND METHOD

This application claims the benefit of U.S. Provisional Application No. 62/030,388 filed Jul. 29, 2014, the content of which is herein incorporated by reference in its entirety.

FIELD OF THE INVENTION

The technology disclosed herein generally relates to implanted leads. More particularly, the technology disclosed herein relates to systems and methods for analyzing implanted leads.

BACKGROUND

Implantable medical devices are commonly used to treat and monitor patients with various medical conditions. Implanted medical devices used in the treatment and monitoring of heart conditions, for example, generally have a hermetically sealed housing that holds at least a power source and processor, as well as one or more leads running from the housing to locations in or about the heart. One or more electrodes along each lead provide electrical sensing and/or stimulating functionality to the heart from the housing.

Over time there can be wear and tear on a lead based on its durability and its environment, which can cause functionality problems such as inaccurate sensing, inaccurate treatment, and the like. As such, it is desirable for caregivers to be able to accurately identify a problematic lead with the information available, while minimizing "false positive" identification of problematic leads.

SUMMARY OF THE INVENTION

One aspect of the technology disclosed herein relates to a method. Implanted medical device data is received, where the medical device data was sensed by a first lead portion and a sensor over a period of time of at least one day. First noise detection criteria are applied to the medical device data sensed by the first lead portion. The number of detected noise events sensed by the first lead portion over the time period is counted based on the first noise detection criteria. Second noise detection criteria is applied to the medical device data sensed by the sensor, and the number of detected noise events over the sensor over the time period is counted based on the second noise detection criteria. The mean number of detected noise events over the time period for the first lead portion and the sensor is calculated, where the mean calculation includes at least the number of detected noise events sensed by the first lead portion and the number of detected noise events sensed by the sensor. A determination of potential lead failure in the first lead is recorded if the number of detected noise events over the first lead over the time period is greater than the mean number of noise events by at least 5%. In one particular example, the time period is at least two weeks.

According to one aspect of the technology, the first noise detection criteria defines a first threshold number of beats that are faster than a first fast beat threshold and the second noise detection criteria defines a second threshold number of beats that are faster than second fast beat threshold, wherein the second fast beat threshold is different than the first fast beat threshold. In one particular example the first threshold number of beats is four beats within an episode. According to another aspect of the technology, a determination of potential electro-magnetic interference is recorded when the number of detected noise events over the first lead is within a margin of the mean number of noise events and the mean number of noise events is above a threshold. According to yet another aspect of the technology, a determination representing potential lead failure in the sensor is recorded if the number of detected noise events over the sensor over the time period is greater than the mean number of noise events.

According to the current technology, the first lead portion and the sensor are different locations along a single lead, or alternatively the first lead portion and the sensor are different leads. In one example the sensor is a right ventricular lead and the second fast beat threshold is 160 milliseconds. In addition or alternatively, the sensor is a left ventricular lead and the second fast beat threshold is 275 milliseconds. In addition or alternatively, the sensor is a right atrial lead and the second fast beat threshold is 110 milliseconds.

Another aspect of the technology disclosed herein relates to a system where an implantable medical device has a plurality of sensors that are configured to sense patient physiological data. The plurality of sensors can have at least one lead. Processing circuitry is configured to receive the patient physiological data and apply noise detection criteria to the patient physiological data sensed by each of the plurality sensors to count the number of noise events over each sensor. In addition or alternatively, the noise detection criteria require at least four beats within an episode to be faster than a threshold. The processing circuitry is also configured to calculate the mean number of noise events from all of the sensors and compare the number of noise events from each lead to the mean number of noise events.

In addition or alternatively, one example system has a user interface in communication with the processing circuitry that is configured to display an alert representing potential lead failure for each lead that had a total number of noise events greater than the mean number of noise events. In addition or alternatively, the user interface is configured to display an alert of potential electro-magnetic interference when the number of detected noise events over a lead is within a margin of the mean number of noise events and the mean number of noise events is above a threshold.

In some aspects of the presently-disclosed technology, the processing circuitry is disposed within the implantable medical device. In addition or alternatively, a portion of the processing circuitry is disposed within the implantable medical device and another portion of the processing circuitry is disposed in a communicator that is configured for communication with the implantable medical device. In one example the processing circuitry is configured to apply different noise detection criteria to each of the sensors. In another example the processing circuitry is configured to receive the patient physiological data that was sensed over a time period of at least two weeks.

According to one aspect of the technology herein, the at least one lead comprises a first lead that is a right atrial lead and the processing circuitry is configured to apply a first noise detection criteria to the first lead that comprises sensing a plurality of sensed beats within an episode that are faster than 110 milliseconds. According to another aspect, the at least one lead comprises a second lead that is a left ventricular lead and the processing circuitry is configured to apply a second noise detection criteria to the second sensor that comprises sensing a plurality of sensed beats within an episode that are faster than 275 milliseconds.

Figure 1:
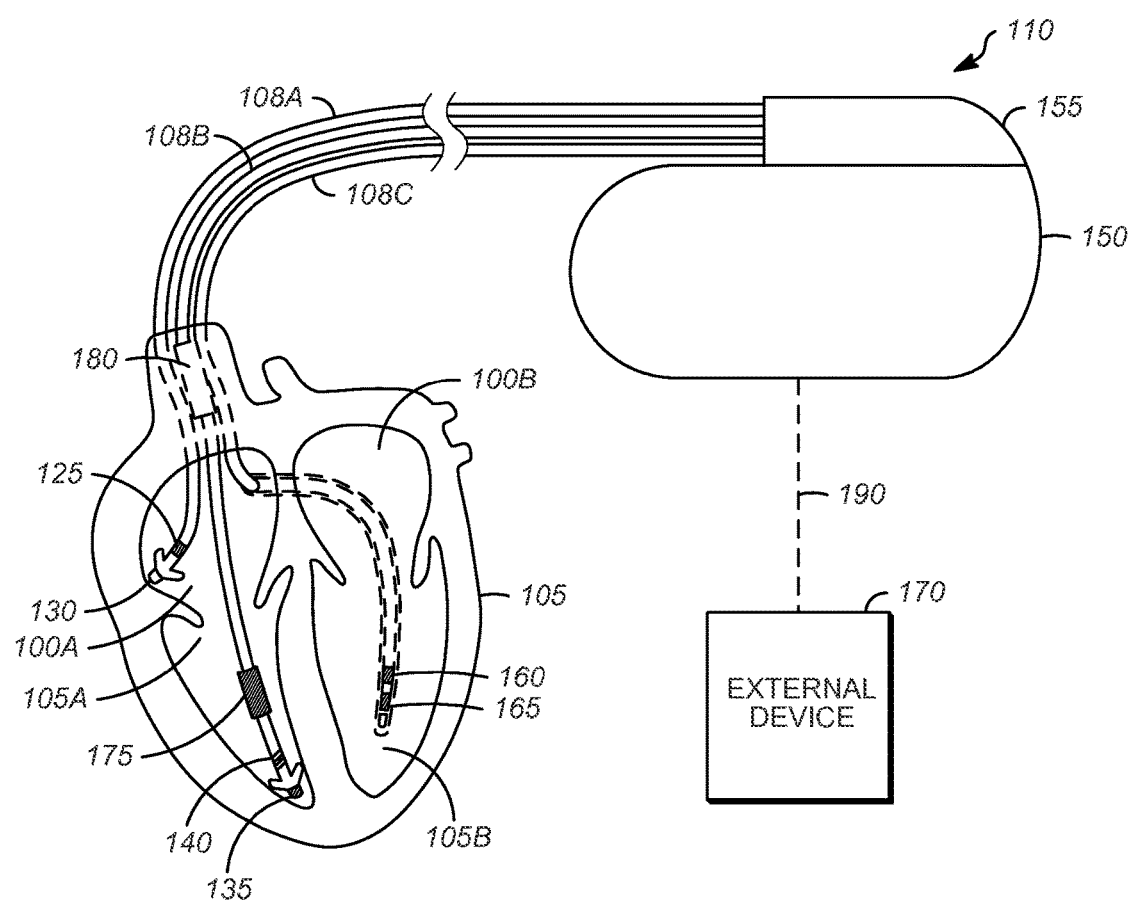
FIG. 1 depicts an example implementation of an implanted medical device, consistent with the technology disclosed herein.

The invention may be more completely understood and appreciated in consideration of the following detailed description of various embodiments of the invention in connection with the accompanying drawings.

DETAILED DESCRIPTION

One aspect of the technology disclosed herein relates to a method. Implanted medical device data is received, where the medical device data was sensed by a first lead portion and a sensor over a period of time of at least one day. First noise detection criteria are applied to the medical device data sensed by the first lead portion. The number of detected noise events sensed by the first lead portion over the time period is counted based on the first noise detection criteria. Second noise detection criteria is applied to the medical device data sensed by the sensor, and the number of detected noise events over the sensor over the time period is counted based on the second noise detection criteria. The mean number of detected noise events over the time period is calculated, where the mean calculation includes at least the number of detected noise events sensed by the first lead portion and the number of detected noise events sensed by the sensor. A determination of potential lead failure in the first lead is recorded if the number of detected noise events over the first lead over the time period is greater than the mean number of noise events by at least 5%. In one particular example, the time period is at least two weeks.

According to one aspect of the technology, the first noise detection criteria defines a first threshold number of beats that are faster than a first fast beat threshold and the second noise detection criteria defines a second threshold number of beats that are faster than second fast beat threshold, wherein the second fast beat threshold is different than the first fast beat threshold. In one particular example the first threshold number of beats is four beats within an episode. According to another aspect of the technology, a determination of potential electro-magnetic interference is recorded when the number of detected noise events over the first lead is within a margin of the mean number of noise events and the mean number of noise events is above a threshold. According to yet another aspect of the technology, a determination representing potential lead failure in the sensor is recorded if the number of detected noise events over the sensor over the time period is greater than the mean number of noise events.

According to the current technology, the first lead portion and the sensor are different locations along a single lead, or alternatively the first lead portion and the sensor are different leads. In one example the sensor is a right ventricular lead and the second fast beat threshold is 160 milliseconds. In another example the sensor is a left ventricular lead and the second fast beat threshold is 275 milliseconds. In yet another example the sensor is a right atrial lead and the second fast beat threshold is 110 milliseconds.

Another aspect of the technology disclosed herein relates to a system where an implantable medical device has a plurality of sensors that are configured to sense patient physiological data. The plurality of sensors can have at least one lead. Processing circuitry is configured to receive the patient physiological data and apply noise detection criteria to the patient physiological data sensed by each of the plurality sensors to count the number of noise events over each sensor. According to one example, the noise detection criteria require at least four beats within an episode to be faster than a threshold. The processing circuitry is also configured to calculate the mean number of noise events from all of the sensors and compare the number of noise events from each lead to the mean number of noise events.

One example system has a user interface in communication with the processing circuitry that is configured to display an alert representing potential lead failure for each lead that had a total number of noise events greater than the mean number of noise events. In addition or alternatively, the user interface is configured to display an alert of potential electro-magnetic interference when the number of detected noise events over a lead is within a margin of the mean number of noise events and the mean number of noise events is above a threshold.

In some aspects of the presently-disclosed technology, the processing circuitry is disposed within the implantable medical device. In addition or alternatively, a portion of the processing circuitry is disposed within the implantable medical device and another portion of the processing circuitry is disposed in a communicator that is configured for communication with the implantable medical device. In one example the processing circuitry is configured to apply different noise detection criteria to each of the sensors. In another example the processing circuitry is configured to receive the patient physiological data that was sensed over a time period of at least two weeks.

According to one aspect of the technology herein, the at least one lead comprises a first lead that is a right atrial lead and the processing circuitry is configured to apply a first noise detection criteria to the first lead that comprises sensing a plurality of sensed beats within an episode that are faster than 110 milliseconds. According to another aspect, the at least one lead comprises a second lead that is a left ventricular lead and the processing circuitry is configured to apply a second noise detection criteria to the second sensor that comprises sensing a plurality of sensed beats within an episode that are faster than 275 milliseconds.

FIG. 1 depicts an example implementation of an implanted medical device (IMD) 110, which is a cardiac rhythm management device. Examples of IMDs 110 include, without limitation, a pacer, a defibrillator, a cardiac resynchronization therapy (CRT) device, or a combination of such devices. The system also typically includes an IMD programmer or other external device 170 that communicates wireless signals 190 with the IMD 110, such as by using radio frequency (RF) or other telemetry signals.

In one embodiment, the external device 170 communicates with the IMD at scheduled intervals to download information from the IMD. In one example, the external device 170 communicates once every 24 hours with the IMD. During a communication session, the IMD uploads information about the patient and any therapy delivered during the time interval since the previous communication session. The downloaded information can include a summary of any episodes that occurred during the time interval or a subset of those episodes, where the summary can include whether a shock was delivered in the episode and notifications and alerts from the IMD. The downloaded information can also be more complete episode data that reflects a substantial portion of the measured physiological data during the episode, where an episode is defined herein as a time period of particular interest, which can be determined according to algorithms stored in the IMD. One example of an episode of particular interest during lead analysis is a tachy episode, where the IMD algorithms indicate that the patient's heart is beating abnormally fast.

The IMD 110 generally has a plurality of sensors that are configured to sense patient physiological data. The sensors include one or more leads 108A-C that are coupled to the heart 105. Cardiac leads 108A-C include a proximal end that is coupled to IMD 110 and a distal end, coupled by an electrode or electrodes to one or more portions of a heart 105. The electrodes typically deliver cardioversion, defibrillation, pacing, or resynchronization therapy, or combinations thereof to at least one chamber of the heart 105. The electrodes may be electrically coupled to sense amplifiers to sense electrical cardiac signals. For purposes of the current application, leads and electrodes disclosed herein will generally be referred to as sensors.

The heart 105 has a right atrium 100A, a left atrium 100B, a right ventricle 105A, a left ventricle 105B, and a coronary sinus extending from right atrium 100A. The atrial lead 108A includes electrodes (electrical contacts, such as ring electrode 125 and tip electrode 130) disposed in the right atrium 100A of heart 105 for sensing signals, or delivering pacing therapy, or both, to the right atrium 100A.

The ventricular lead 108B includes one or more electrodes, such as tip electrode 135 and ring electrode 140, for sensing signals, delivering pacing therapy, or both sensing signals and delivering pacing therapy. The lead 108B optionally also includes additional electrodes, such as for delivering atrial cardioversion, atrial defibrillation, ventricular cardioversion, ventricular defibrillation, or combinations thereof to the heart 105. Such electrodes typically have larger surface areas than pacing electrodes in order to handle the larger energies involved in defibrillation. The lead 108B optionally provides resynchronization therapy to the heart 105.

The IMD 110 may include a third cardiac lead 108C attached to the IMD 110 through the header 155. The third cardiac lead 108C includes ring electrodes 160, 165 placed in a coronary vein lying epicardially on the left ventricle (LV) 105B via the coronary vein.

The lead 108B may include a first defibrillation coil electrode 175 located proximal to tip and ring electrodes 135, 140 for placement in a right ventricle (RV), and a second defibrillation coil electrode 180 located proximal to the first defibrillation coil 175, tip electrode 135, and ring electrode 140 for placement in the superior vena cava (SVC). In some examples, high-energy shock therapy is delivered from the first or RV coil 175 to the second or SVC coil 180. In some examples, the SVC coil 180 is electrically tied to an electrode formed on the hermetically-sealed IMD can 150. This improves defibrillation by delivering current from the RV coil 175 more uniformly over the ventricular myocardium. In some examples, the therapy is delivered from the RV coil 175 only to the electrode formed on the IMD can 150.

Other forms of sensors include meshes and patches which may be applied to portions of heart 105 or which may be implanted in other areas of the body to help "steer" electrical currents produced by IMD 110. The present methods and systems will work in a variety of configurations and with a variety of sensors. Sensing among different sets of electrodes often provides directional information regarding the propagation of cardiac signals and is often referred to as sensing among different vectors. For example, in a single chamber ICD, sensing from a right ventricular tip electrode 135 to a right ventricular ring electrode 140 would be a first vector, and sensing from an RV coil 175 to an electrode on the can 150, or a header 155, would be second vector. Various electrode configurations may be used.

The sensor configuration used in the systems and methods described herein allow for the collection of patient episode data including electrograms (EGMs) on at least the right ventricular channel, while multiple channels may be used. The right ventricular EGM signal is recorded with electrodes implanted in or near a ventricle. For example, a ventricular channel or vector may include a tip electrode and ring electrode for the right ventricular channel or ring electrodes for the left ventricular channel. Another channel, known as the shock channel or shock vector, may be used. The shock channel is sensed using electrodes that are also used to deliver high-energy shock therapy. In one example, the shock channel includes an electrode placed in the RV.

Figure 10:
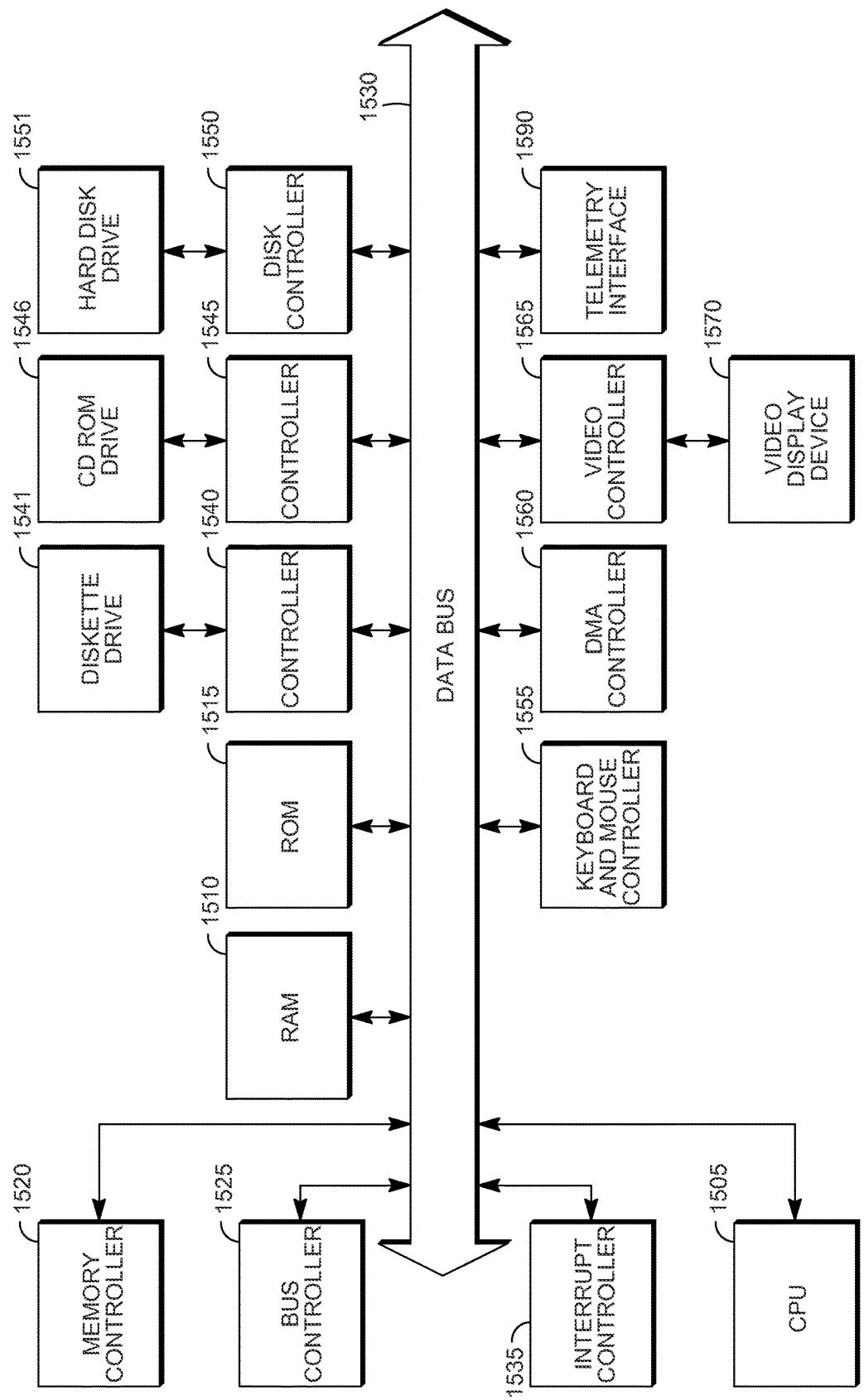
FIG. 10 depicts a schematic of various components consistent with some embodiments of the technology disclosed herein.

As will be described with reference to FIG. 10, the IMD has a processor having processing circuitry and memory to store patient episode data to be uploaded by a communication module. The IMD can overwrite the memory as necessary to store new patient episode data.

As will be appreciated by those having skill in the art, over the life of the patient the leads 108A-108C can experience general wear and tear impacted by their durability and their environment. Such wear and tear can cause functionality problems such as inaccurate sensing, inaccurate treatment, and the like. As such, it can be desirable for caregivers to be able to accurately identify a problematic lead with the information available, while minimizing "false positive" identification of problematic leads.

The sensing of signals by the IMD 110 may be susceptible to noise. In a general sense, noise refers to irregular fluctuations that accompany a transmitted electrical signal but are not part of it and may obscure it. There are many examples of specific and technical definitions of signal noise in different contexts. Signal noise may be physiologic or non-physiologic in nature. Noise may be due to the device itself, such as due to fracture of an IMD lead, or a faulty set screw or adapter used for securing an IMD lead. Alternatively, signal noise may be due to externally-caused electronic "chatter" picked up by the IMD lead, which can be referred to as electromagnetic interference (EMI). Sources of EMI include electrocautery during surgery, magnetic resonance imaging, a lithotripsy procedure, or transmissions from electronic surveillance equipment, such as found at store entrances or security gates. There are many other sources of signal noise as well. EMI is one of the most common sources of signal noise. Distinguishing between noise cause by EMI and noise caused by problems with the device, such as a faulty lead, can minimize the false positive identifications of problematic leads.

Figure 2:
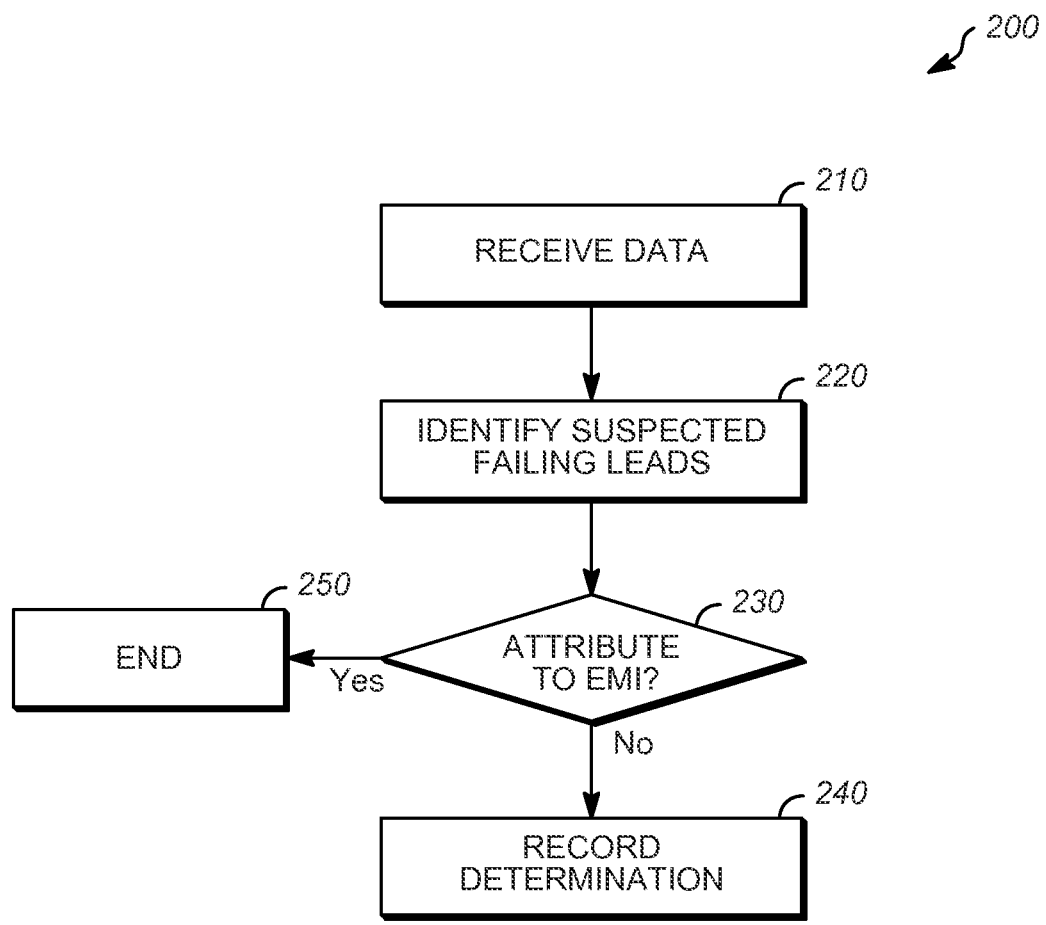
FIG. 2 depicts a high level schematic of one method consistent with the technology disclosed herein.

FIG. 2 depicts a high level schematic of noise analysis 200 consistent with the technology disclosed herein. The system receives data 210 and identifies any suspected failing leads 220 based on sensing noise in the received data 210 from the lead. If the system is able to attribute the lead noise to electromagnetic interference 230, the analysis ends 250. If the system does not attribute the lead noise to electromagnetic interference 230, the system records the determination 240 of the potentially failing lead. In one example, the system alerts the user to the potentially failing lead.

The analyses described herein are generally conducted with one or more processing modules having processing circuitry. The processing circuitry can be disposed within the IMD, or can be external to the IMD. In some embodiments the processing circuitry is distributed across a number of system components including the IMD and an external programmer, for example. As an example embodiment, a portion of the processing circuitry can be disposed within the implantable medical device and another portion of the processing circuitry is disposed in a communicator that is configured for communication with the implantable medical device. In a variety of embodiments, the lead is an implanted lead consistent with an implanted cardiac rhythm management device depicted in FIG. 1.

The alert can generally be consistent with that known in the art through a patient and/or caregiver system interface, e-mail, and the like. The alert will generally be accomplished by one or more alert modules having relevant processing circuitry. Where the analysis is performed in the external device that prompts the alert, the alert will generally be in real time immediately subsequent to the analysis being performed and include a timestamp of the episode that triggered the alert. The system can also be configured to store the notification and timestamp and analyze data based on the timestamp, and other data associated with each alert, which can be referred to as an alert record.

Where an analysis leading to a determination or an alert is performed by the IMD, the determination, the alert or both can be part of the episode summary information that is downloaded to the external device during a communication session.

Figure 3:
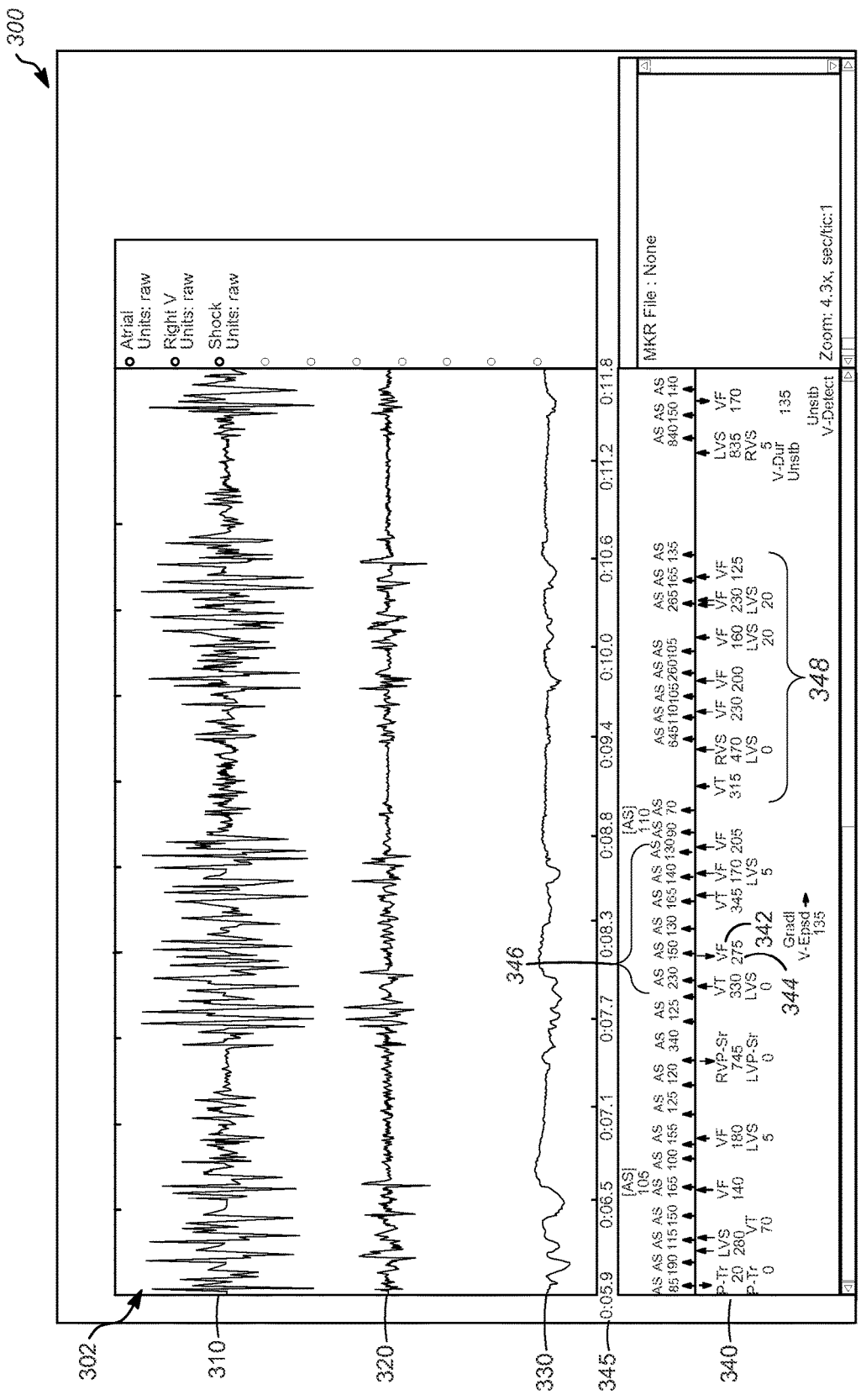
FIG. 3 depicts a portion of an example episode data record.

FIG. 3 depicts a particular episode data record 300 that has an electrogram (EGM) portion 302 and an associated marker portion 340. Generally, an IMD consistent with the currently-described technology determines locations of heart beats within the EGM data 302, resulting in a group of device-identified beat locations that are device markers 340. The EGM portion 302 is generally a graphical representation of the patient's cardiac activity and the marker portion 340 marks detected events corresponding to the EGM portion 302. The EGM data 302, in the current embodiment, depicts sensed atrial data 310, sensed right ventricular data 320, sensed shock channel data 330, and a timestamp 345. Among other data, the marker portion 340 can indicate beat-specific data such as the heartbeat zone 342, heartbeat duration 344, pacing therapy (not shown), diverted shock (not shown), and event detection, as examples. Examples of heartbeat zone data 342 include ventricular tachycardia (VT), ventricular fibrillation (VF). Those having skill in the art will appreciate the other types of marker data 340 that can be provided.

The EGM data 302 and markers 340 are stored in a memory of the IMD. A communication module can initiate retrieval of the episode data record 300 for an episode from the IMD. The episode data 300 is then analyzed in the noise analysis 200 of FIG. 2, which is described in more detail with reference to FIG. 7. In one embodiment, the noise analysis 200 utilizes the marker portion 340 of the episode data record and does not utilize the EGM portion 302 of the episode data record. In one example, the noise analysis 200 utilizes both the marker portion 340 and the EGM portion 302 of the episode data record. In one example, the noise analysis 200 utilizes the EGM portion 302 of the episode data record and not the marker portion 340 of the episode data record.

Figure 4:
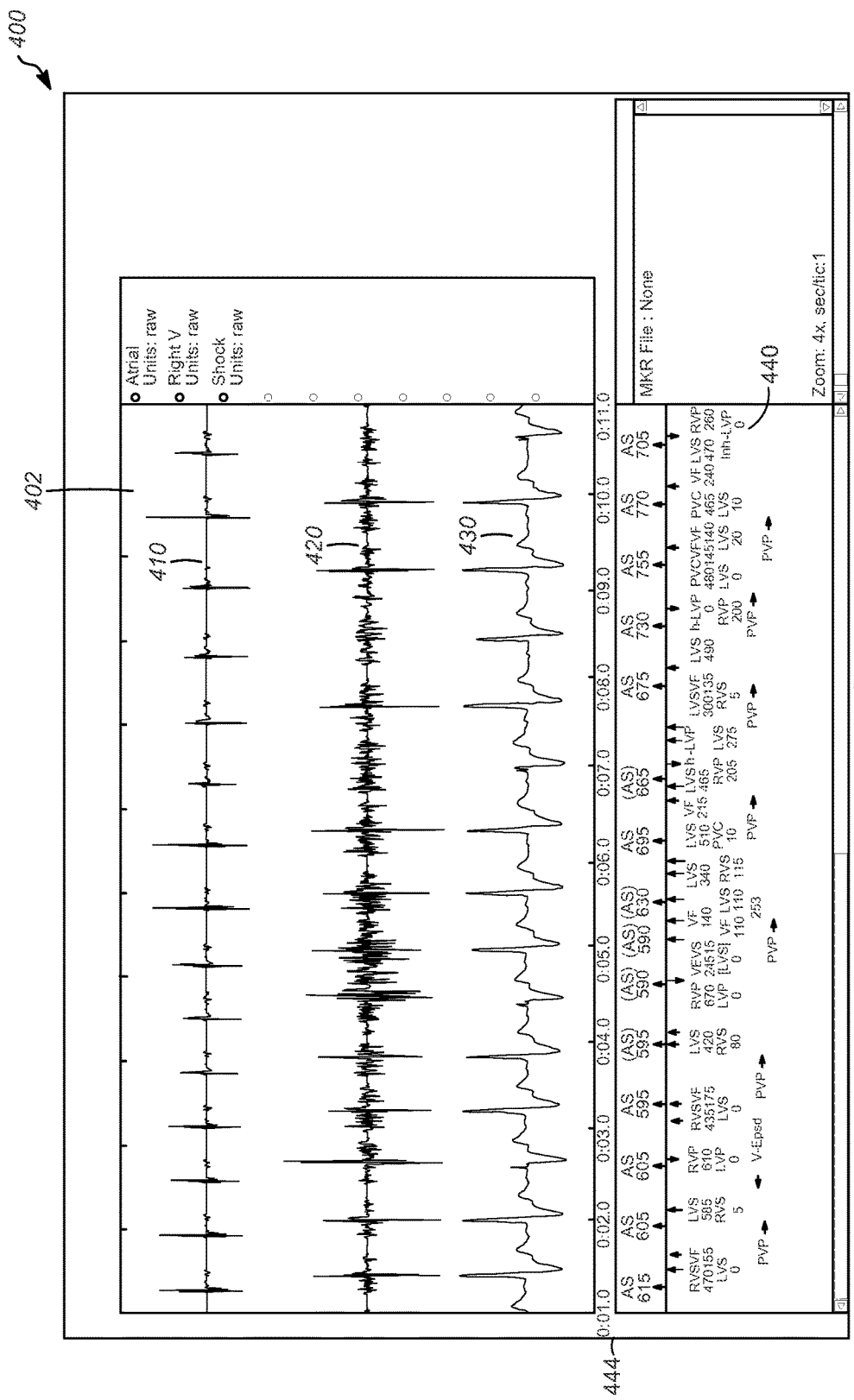
FIG. 4 depicts a portion of another example episode data record.

FIG. 4 similarly depicts an example episode record 400 having an EGM portion 402 conveying data associated with the atrial channel 410, right ventricular channel 420, and the shock channel 430. The example episode record 400 includes a timestamp 444. The episode record 400 also has a marker portion 440 that summarizes the data from the EGM portion 402.

Both episode data records 300, 400 have evidence of non-physiologic noise in the EGM portions 302, 402 because there are irregular fluctuations of the signal that appear to be independent from the cardiac rhythms that are being sensed. A trained observer will conclude that the episode data record 300 of FIG. 3 is a result of electromagnetic interference, since there is evidence of noise present on all the EGM channels. A trained observer will conclude that the episode data record 400 of FIG. 4 depicts episode data 400 demonstrating a potentially failing right ventricular lead. The episode data 300 depicted in FIG. 3 in the EGM portion 302 generally appears to be inconsistent with actual patient physiometry across each of the atrial 310, ventricular 320, and shock 330 channels. Indeed the marker portion 340 of the episode data record 300 reflects that multiple sensed beats on the atrial marker channel 346 and the right ventricular marker channel 348 are faster than what is generally considered to be physiologically possible. On FIG. 4, however, the EGM portion 402 of the episode data record 400 generally shows EGM data consistent with actual patient physiological beats along the atrial 410 and shock channels 430, but along the right ventricular channel 420 the EGM data appears to be inconsistent with an actual physiological response. As such, one conclusion that could be drawn is that the right ventricular lead is failing and may need to be replaced.

The system according to the technology disclosed herein is generally configured to distinguish between the scenarios depicted in FIGS. 3 and 4. Specifically, the system is configured to identify suspected failing leads through a noise analysis, which has the technical effect of reducing the false positives that arise when noise is detected from electromagnetic interference.

Figure 5:
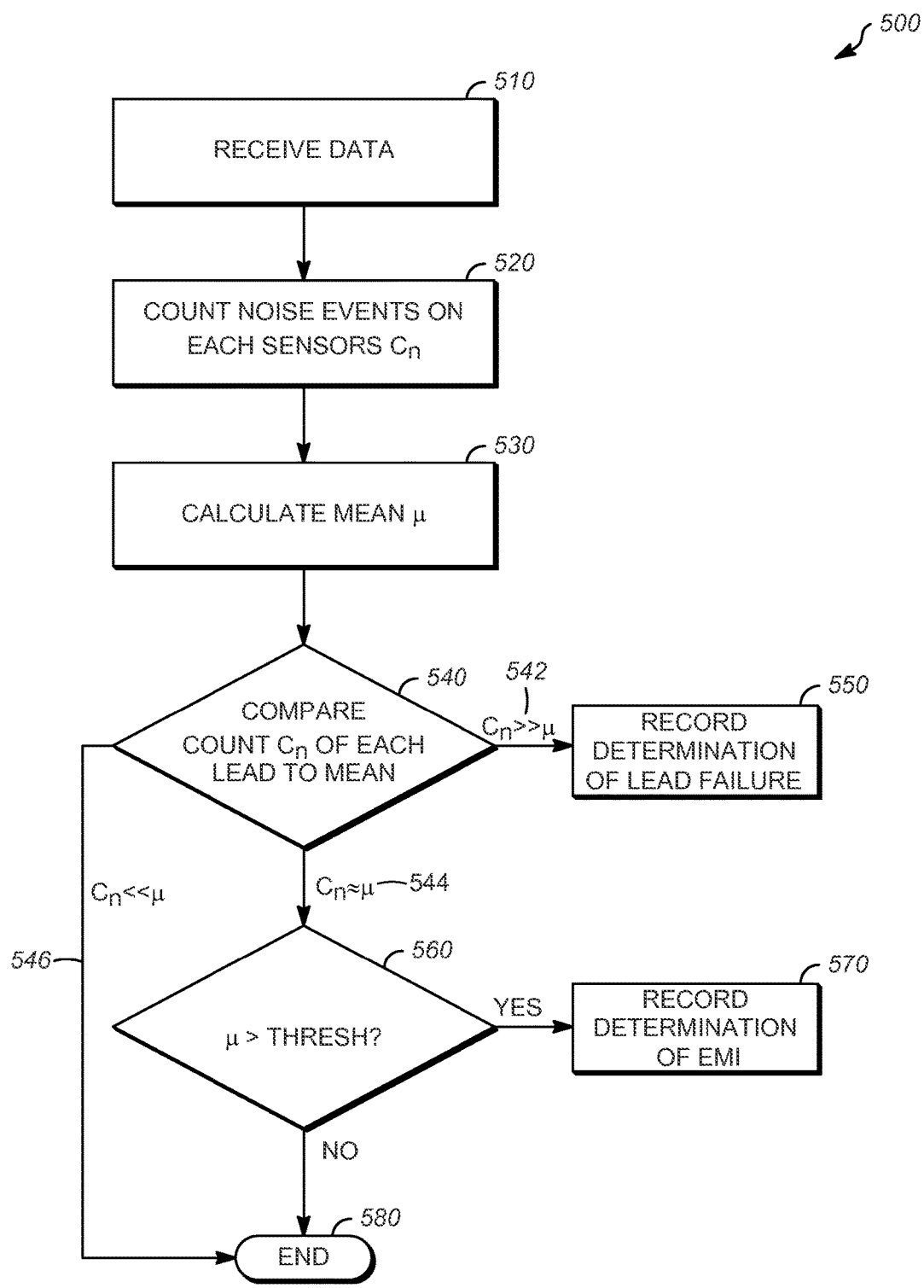
FIG. 5 depicts an example schematic associated with the technology disclosed herein.

FIG. 5 depicts an example schematic associated with an embodiment of the technology disclosed herein. Data is received 510 from IMD sensors and the noise events are counted from each sensor 520. The mean number of detected noise events over all of the sensors is calculated 530. Then, the count of noise events from each sensor is compared to the mean 540. At least one of the sensors is a lead or a portion of a lead. If a sensor is a lead or a portion of a lead, and if that sensor has a number of noise events are greater than the mean 542, then the system generates a determination of potential lead failure 550. In one example, the system generates an alert of potential lead failure. If the number of noise events is about equal to the mean 544, the system conducts an analysis to determine whether the mean is above a threshold 560 and, if the mean is above the threshold, then the system generates a determination of electromagnetic interference 570. In one example, the system generates an alert of electromagnetic interference. If the number of noise events is below the mean 546, or the mean is not above the threshold 560, then the analysis ends.

The IMD data that is received 510 is generally patient physiological data sensed by each of the plurality of medical device sensors. The medical device data generally will have been sensed by the sensors over a period of time of at least one day in one embodiment, at least two weeks in another embodiment, and at least thirty days in yet another embodiment. The term "sensor" is used to describe a variety of medical device components that can sense patient electrophysiometry, but generally the sensors that are analyzed for potential failure are leads. Other sensors such as non-lead electrodes can be analyzed for noise, however, as a basis for comparison to the leads being analyzed. Non-lead electrodes can be positioned on an exterior surface of the IMD or in other locations. Different sensors can be different portions of a single lead or different leads altogether. The term "sensor" are used herein refers to a sensor of electrical potential.

The processing circuitry of the system is generally configured to count noise events $C_n$ on each sensor 520 by applying noise detection criteria to the medical device data sensed by each sensor over the particular time period, which will be described below with reference to FIG. 6. The letter "n" indicates the number of the sensor used to count the noise events, such that $C_1$ indicates the noise events counted at a first sensor during the time period, $C_2$ indicates the noise events counted at a second sensor during the time period, $C_3$ indicates the noise events counted at a third sensor during the time period, etc. The total number of sensors could be as few as two. In one example, there are three sensors used to count noise events. In another example there are four sensors used to count noise events. Generally each sensor can have particular noise detection criteria that will apply to the particular sensor, depending on how sensed physiological measurements from that sensor can be distinguished from sensed non-physiological noise from that sensor. The total number of noise events $C_n$ sensed by each sensor is used to determine the mean μ number of noise events 530 over all of the sensors over the time period, where calculating the mean number of noise events 530 will generally be appreciated by those having skill in the art. To calculate the mean over all the sensors over the time period, the number of noise events over the time period detected at each sensor is added together and then divided by the total number of sensors over which noise events were detected.

The system records a determination of potential lead failure 550 if a lead has a detected number $C_n$ of noise events over the time period that is greater than the mean μ number of noise events by a particular threshold amount, for example where the number of noise events $C_n$ is greater than 5%, greater than 10%, or greater than 20% of the mean μ. In at least one embodiment, the particular threshold amount can vary depending on the configuration of the particular lead. The determination can generally represent potential lead failure of the particular lead that had a total number of noise events $C_n$ greater than the mean number of noise events μ. In some examples, an alert is generated of potential lead failure after the determination is recorded. The alert can be displayed through a user interface, as has been described herein, which is in communication with system processing circuitry.

The number of noise events $C_n$ sensed by a lead is about equal to the mean μ 544 generally if the number of sensed noise events $C_n$ is within a margin of the mean μ number of noise events, where the margin can be at least 15%, 10%, or even 5% of the mean μ. In such a scenario it can be unlikely that the lead is experiencing failure because the noise that is detected is within the range of the mean μ number of noise events so the conclusion that can be drawn is that an external source of EMI is causing a similar level of noise on all of the sensors. If the mean μ number of noise events is particularly high across multiple leads, that is, if the mean number of noise events is above an EMI threshold 560, the system is configured to generate and record a determination of potential EMI 570. In one example, the system is configured to generate an alert of potential electromagnetic interference. Attention is drawn back to FIG. 3, for example, where a high number of noise events are identifiable on the atrial lead data 310 and the right ventricular lead data 320.

If the number of noise events $C_n$ for a lead is below the mean 546 (outside of the margin), or the mean μ is not above the EMI noise threshold 560, then the analysis will generally end. In particular, a lead that has sensed a number of noise events $C_n$ below the mean μ number of noise events is generally not exhibiting characteristics associated with lead failure. Furthermore, if the mean μ is not above the EMI noise threshold 560, the medical device system is generally not being exposed to a notable or significant amount of electromagnetic interference. As such, the system analysis ends 580.

Figure 6:
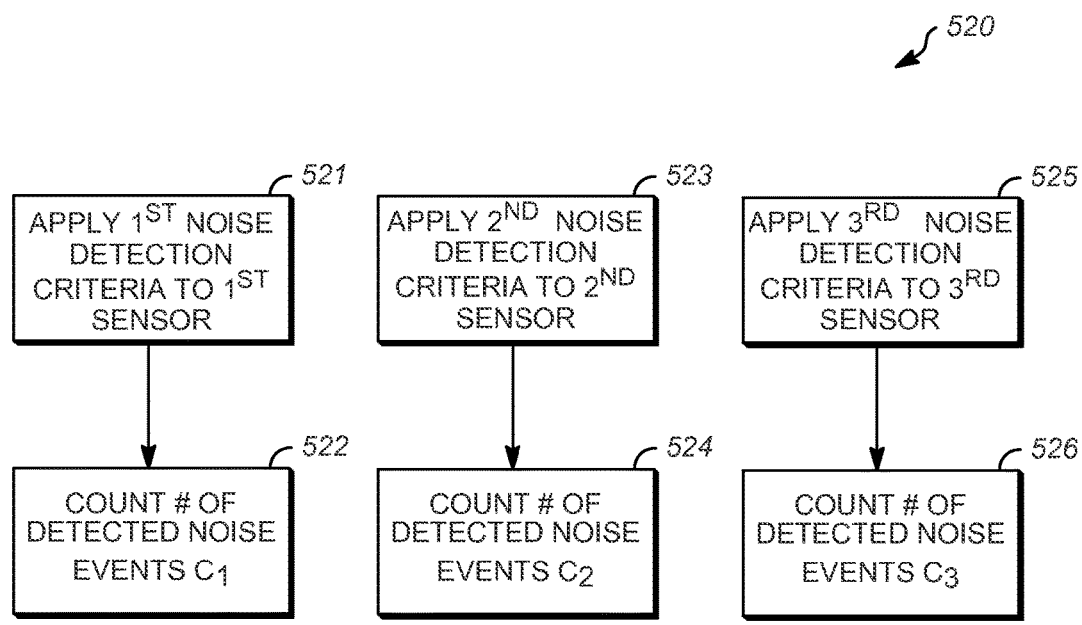
FIG. 6 depicts another example schematic associated with the technology disclosed in FIG. 5.

FIG. 6 depicts one example of counting the number of noise events on each sensor 520 from FIG. 5. In the example, the medical device has at least a first sensor, a second sensor, and a third sensor. The processing circuitry is configured to apply first noise detection criteria to the medical device data that was sensed by the first sensor 521 over a time period, and then count the number of detected noise events sensed by the first sensor 522 based on the noise detection criteria $C_1$ 521. The processing circuitry is also configured to apply second noise detection criteria to the medical device data that was sensed by the second sensor 523 over the time period, and count the number of detected noise events sensed by the second sensor $C_2$ 524 based on the second noise detection criteria 523. Similarly, the processing circuitry is configured to apply third noise detection criteria to the medical device data that was sensed by the third sensor 525 over the time period, and count the number of detected noise events sensed by the third sensor $C_3$ 526 based on the third noise detection criteria 525. Data from additional sensors or fewer sensors could also be processed by the system.

Generally, at least one of the first sensor, the second sensor and the third sensor will be a lead that is being analyzed for failure by the system. In such an embodiment the lead is particularly a portion of a lead that is being analyzed by the system. In some embodiments another sensor can be a different location along the same lead or it could be a portion of a different lead. As will be described in more detail with reference to FIG. 7, the first noise detection criteria can define a first threshold, the second noise detection criteria can define a second threshold, and the third noise detection criteria can define a third threshold. The processing circuitry will generally apply thresholds dependent on the type of sensor used and, as such, the first threshold, second threshold, and third threshold are not necessarily the same. Indeed, in at least one embodiment, each of the first threshold, second threshold, and third threshold are different.

Figure 7:
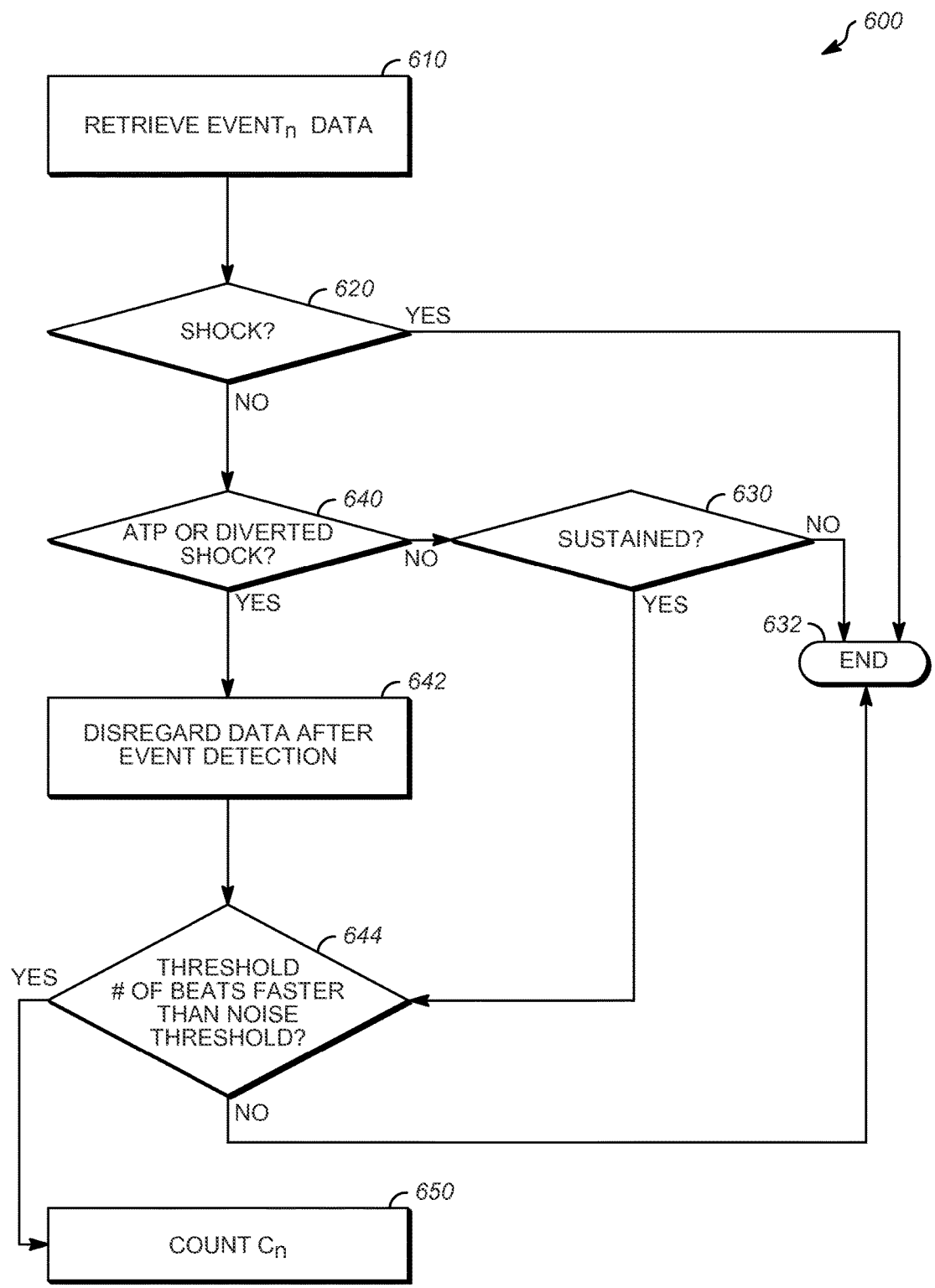
FIG. 7 depicts an example schematic associated with noise analysis for a sensor.

FIG. 7 depicts an example schematic associated with counting a noise event from a sensor, where this particular process would be used for each event from each sensor. The episode data for each episode retrieved 610 is processed to identify whether a shock was delivered 620 during that episode. If a shock is identified 620, no noise is counted and the analysis ends 632. The system also considers whether anti-tachycardia pacing (ATP) was administered or a shock was diverted 640. If so, data after the event is disregarded 642 and a fast beat threshold test is applied 644 to the data before the event. If the episode data meets the fast beat threshold criteria 644, the event is counted in the total number of noise events 650. If no ATP was administered or shock diverted 640, the event data is examined to identify whether the event was sustained 630. If so, the fast beat threshold test is applied 644 and, if the episode data meets the fast beat threshold test, the episode is counted in the total number of noise events 650. Otherwise, the episode is not counted and the analysis ends 632. Similarly, if the episode was not sustained 630, the episode is not counted in the total number of noise events and the analysis of that event ends 632.

Generally, episode data where shock was administered 620 is not considered in the total count of noise events. In a variety of systems, episodes resulting in the administration of a shock 620 to a patient are currently afforded a relatively high level of scrutiny based on the high impact of the shock on the patient and the potentially dangerous physiological state experienced by the patient. Further, administration of an improper shock treatment to the patient is typically examined with haste after the occurrence. As such, analysis for noise associated with episodes leading up to a shocked treatment might often be redundant. In one alternate embodiment, however, episodes where a shock was administered can be considered in noise analysis.

Identification of ATP 640 can include considering the EGM markers from the episode data for a marker that indicates ATP. Similarly, identification of a diverted shock 640 can include considering the EGM markers from the episode data for a marker that indicates a diverted shock. In some embodiments, episodes with ATP or a diverted shock are identified by a marker in the episode data that marks an event detection resulting in the ATP or diverted shock. An event detection marker or "detection met" marker indicates that the IMD has decided that a cardiac event has occurred, according to the IMD's programmed criteria, which warrants that some type of therapy be provided to the patient. Examples of therapy that can be provided to the patient include shock or ATP, among others. In some situations, the criteria for a shock is satisfied by the sensed physiological data, resulting in an event detection marker, and the IMD initiates charging to deliver a shock, but the IMD decides not to deliver the shock and so diverts the shock. In some embodiments, these episodes will have a marker indicating that the shock was diverted.

If the episode data includes a marker for either ATP or diverted shock 640, a noise analysis is conducted that disregards the episode data after the event detection 642. In a variety of instances, administered therapy can cause particularly fast heart beats that may be interpreted by the system as "noise." As such, it may improve the predictive value of the system to ignore such data. Additionally, focusing on physiological data that triggers an event detection to warrant a diverted shock can allow a system user to improve system analytics.

In the current embodiment the system is configured to only analyze sustained episodes 630 to count as a noise event. Indeed, in a variety of systems, non-sustained episodes are not considered in the noise analysis 600 to conserve system resources such as IMD battery life and processing bandwidth. This is because non-sustained episodes generally occur at a relatively high frequency when compared with sustained episodes. For purposes of this application, a "sustained episode" is defined as an episode that meets minimum time requirements. For example, a "sustained episode" may be defined in one embodiment as where eight out of ten beats are faster than a programmed rate threshold and then six out of ten beats remain faster than the programmed rate threshold, which is maintained for a programmed length of time.

Generally the programmed length of time can range from about 1 second to about 60 seconds and the programmed rate threshold can range from about 160 beats per minute (bpm) to about 200 bpm. In a variety of embodiments the programmed length of time ranges from about one second to about 2.5 seconds. In some embodiments the programmed length of time is one second. In some embodiments the programmed length of time is two seconds. In some embodiments the programmed length of time is up to sixty seconds. In some embodiments the programmed rate threshold is 160 bpm. In some embodiments the programmed rate threshold is 180 bpm. In some embodiments the programmed rate threshold is 200 bpm. The programmed rate threshold can be dependent on the particular sensor being analyzed, and is generally different than the fast beat threshold, which will now be described.

The fast beat threshold test 644 determines whether the episode meets the noise detection criteria that determine whether the episode should be counted as a noise episode 650. Particularly, the fast beat threshold analysis 644 determines whether there are a threshold number of beats that are each faster than the beat length (noise) threshold 644. In at least one embodiment, the threshold number of beats is four. The processing circuitry of the system disclosed herein is generally configured to apply different noise detection criteria depending on the sensors being analyzed. In particular, the beat length threshold generally depends on the particular sensor used. In one embodiment, the fast beat threshold for an atrial lead is about 110 milliseconds, about 275 milliseconds for a left ventricular lead, and about 160 milliseconds for a right ventricular lead.

So, in one example using a left ventricular lead, the noise detection criteria 644 are satisfied if the system identifies at least four beats that are 160 ms or less in length. Those having skill in the art will recognize other numbers of beats occurring at alternate beat length thresholds may also be accurate predictors of noise from a lead.

The analysis for untreated sustained episodes 630 is similar to the analysis of episodes with ATP or diverted shock 640 in that the episode data is evaluated to identify a threshold number of beats that are faster than a threshold beat length 644. If the threshold criteria 644 are met to indicate that the episode was noise, the episode is added to the count $C_n$ of noise events within the time period.

In a variety of embodiments, the system is configured to store the outcomes associated with the application of noise detection criteria to retrieved episode data records. It is noted that FIG. 7 depicts one example embodiment of detecting a noise event, and those having skill in the art will appreciate that there are a variety of other approaches to detecting a noise event from patient physiological sensor data. Further many modifications could be made to the process depicted in FIG. 7 without deviating from the scope of the technology disclosed herein.

In one embodiment of a method related to the current technology the system is configured to compare a first noise detection criteria to first episode data from a first lead at a first time and identify noise in the first lead as a result of the comparison. The system is also configured to compare second noise detection criteria to second episode data from a second lead at a second time, where the second noise detection criteria can be different than the first noise detection criteria. If noise is identified on both of the leads, then potential lead failure can be ruled out by the system, because the noise is likely caused by a factor impacting both of the leads (such as electromagnetic interference). If noise is identified in one lead but not another lead, then the system can generate a determination of potential lead failure of the lead on which noise was identified. For example, if the system identifies a lack of noise in the second lead as a result of the comparison of the second noise detection criteria to the second episode data, then the system can record a determination of potential lead failure of the first lead. In a variety of embodiments the system can be further configured to generate an alert representing the potential lead failure of the first lead.

In some embodiments, the second time can be different than the first time, meaning that the noise on the first lead and the noise on the second lead do not have to be synchronous for the system to identify potential electromagnetic interference, thereby ruling out potential lead failure. Those having skill in the art will appreciate, however, that noise on the first lead and the noise on the second lead certainly can be synchronous for the system to identify potential electromagnetic interference. In some embodiments, the first time and the second time can be within 5 seconds of each other, within 2 seconds of each other, or within 1 second of each other.

Similar to other embodiments described herein, the first criteria and the second criteria can be appropriate for identifying noise over the relevant lead. As such, the first criteria and the second criteria can be different criteria depending on the type of lead and the cardiac location of the lead. In some embodiments the first criteria is a first fast beat threshold and the second criteria can be a second fast beat threshold. The particular value of the first and second fast beat thresholds can be similar to those previously described herein and can require a threshold number of consecutively-sensed beats that are faster than the threshold value. Other approaches for identifying noise on a lead can also be used, such as off-line sensing algorithms. In at least one embodiment the system can conduct an interval analysis to check for regularity of the noise over each of the leads, which can also be an indicator of electromagnetic interference.

Description of Hardware Systems

The above-described method can be implemented on various hardware systems, such as on a programmer, in a patient management system, or other computational devices.

Figure 8:
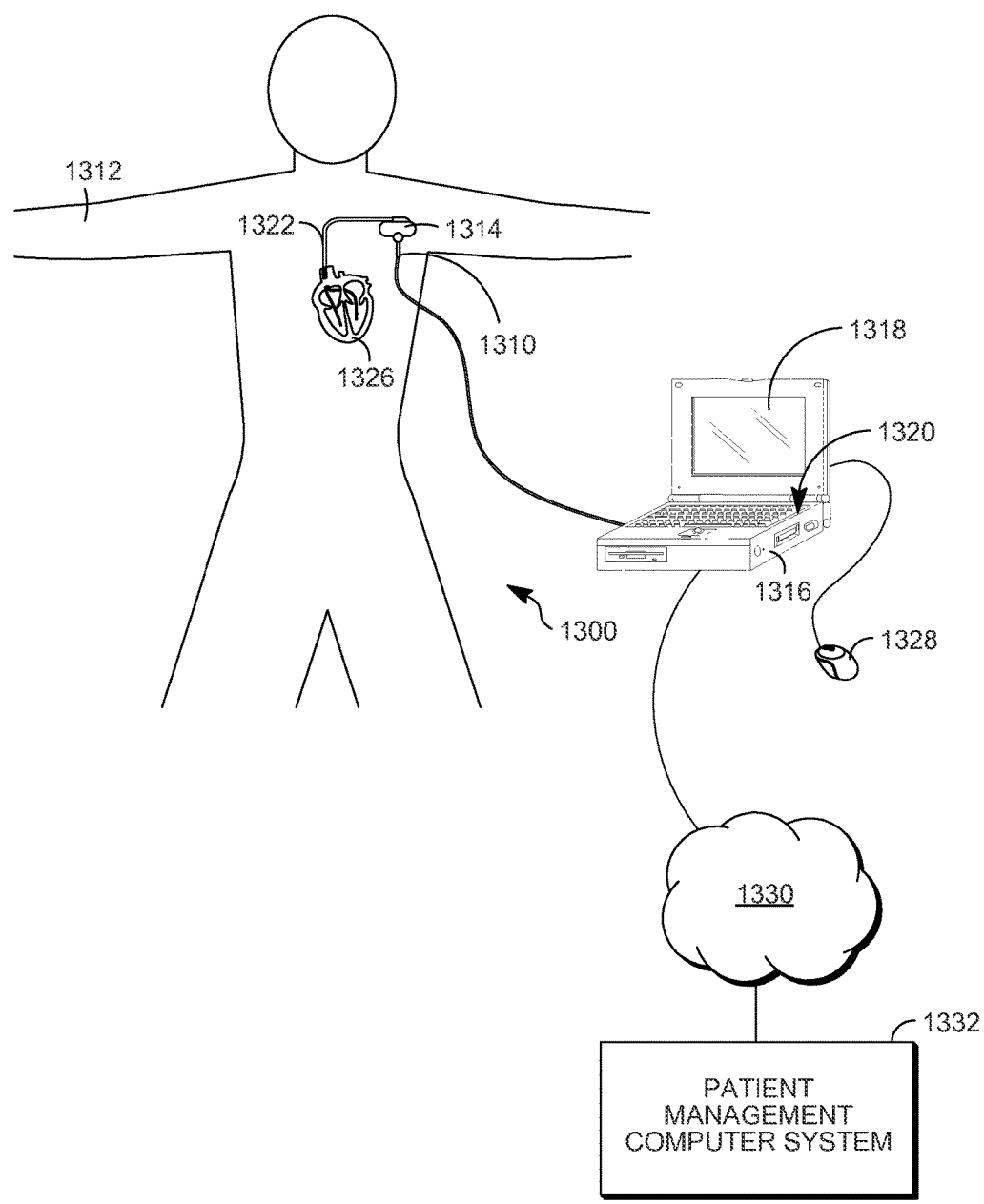
FIG. 8 depicts an example cardiac rhythm management system consistent with at least one implementation of the technology disclosed herein.

FIG. 8 is a schematic of an exemplary cardiac rhythm management (CRM) system 1300. The system 1300 can include an IMD 1314 disposed within a patient 1312. The IMD 1314 can include pacing functionality. The IMD 1314 can be of various types of devices such as, for example, a pacemaker, a cardioverter-defibrillator, a cardiac resynchronization device, a heart rhythm monitoring device, or the like. The IMD 1314 includes one or more leads 1322 disposed in or near the patient's heart 1326.

The IMD 1314 can be in communication with an external interface device 1316. In some embodiments, communication between the IMD 1314 and the external interface device 1316 can be via inductive communication through a wand 1310 held on the outside of the patient 1312 near the IMD 1314. However, in other embodiments, communication can be carried out via radio frequency transmission, acoustically, or the like. The particular device that is configured to retrieve data, including patient data, from the IMD 1314 is generally referred to as a "communication module."

The IMD 1314 can include one or more implanted sensors in order to gather data regarding the patient 1312. For example, the IMD 1314 can include an activity level sensor, a respiration sensor, a heart sounds sensor, a blood pressure sensor, an impedance sensor, or other sensors. The data gathered using the IMD 1314 may be any type of patient data. In a variety of embodiments, and as described above, the IMD 1314 collects electrograms from the patient. The patient data can further comprise data regarding the locations of heart beats within the electrograms. This data can be collected into groups of device-identified beat locations for each collected electrogram.

The IMD 1314 is generally configured to store data over a period of time, and periodically communicate with the external interface device 1316 in order to transmit some or all of the stored data.

The external interface device 1316 can be for example, a programmer, a programmer/recorder/monitor device, a computer, a patient management system, a personal digital assistant (PDA), or the like. As used herein, the term programmer refers to a device that programs implanted devices, records data from implanted devices, and allows monitoring of the implanted device. Exemplary programmer/recorder/monitor devices include the Model 3120 Programmer, available from Boston Scientific Corporation, Natick, Mass. The external interface device 1316 can include a user input device, such as a keyboard 1320 and/or a mouse 1328. The external interface device 1316 can include a video output channel and video output device, such as a video display 1318 for displaying video output. The displayed video output can include a user interface screen. In addition, the video display 1318 can also be equipped with a touch screen, making it into a user input device as well.

The external interface device 1316 can display real-time data and/or stored data graphically, such as in charts or graphs, and textually through the user interface screen. In addition, the external interface device 1316 can present textual information to a user along with several response options. The external interface device 1316 can also input and store a user's response to a question, and can store a user's text response in some embodiments.

In one embodiment, the external interface device 1316, which can also be referred to as a user interface, is in communication with a patient management computer system 1332. The communication link between the user interface 1316 and the patient management computer system 1332 may be via phone lines, the Internet 1330, or any other data connection. The user interface 1316 can also be used when it is not in communication with a device, but is only in communication with the patient management computer system 1332.

In one embodiment, the external interface device 1316 is capable of changing the operational parameters of the IMD 1314, and is therefore referred to as a programmer. Typically, programmers are used to interface with CRM devices in a clinic or hospital setting. In this context, the user of the external interface device 1316 is a physician or trained technician.

The components that execute the analysis as described herein are generally referred to as the "processing circuitry." Those having skill in the art will appreciate that the processing circuitry can include components of the patient management system 1332, the external interface device 1316, other devices, and combinations thereof. Similarly, the components of the system that generate notifications consistent with the technology disclosed herein are generally and collectively referred to as the "notification module," for purposes of this application. In a variety of embodiments the processing circuitry and the notification module are in communication, and in some embodiments the processing circuitry and the notification module have mutual components.

Figure 9:
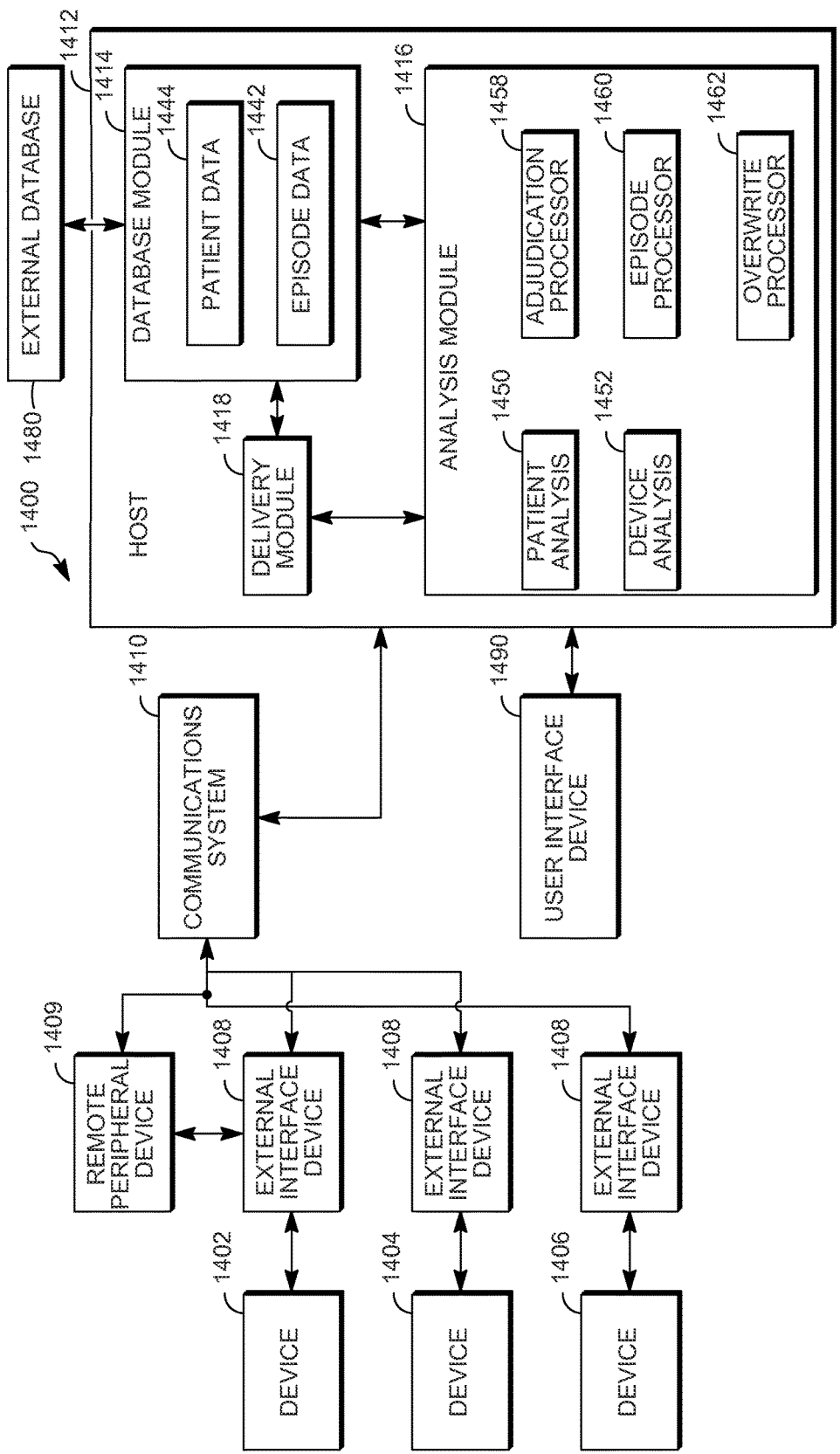
FIG. 9 depicts a schematic of a patient management system consistent with at least one implementation of the technology disclosed herein.

FIG. 9 is a schematic illustration of a patient management system consistent with at least one embodiment of the invention. The patient management system is capable of maintaining an episode database using computer storage medium. Of note, the episode database may also be present in an implantable or implanted device. A computer storage medium is any technology, including devices and materials, used to place, keep and retrieve data. Examples of computer storage medium include random-access memory (RAM), a network-attached storage device, magnetic storage such as hard disk drives, optical discs, and a redundant array of independent discs (RAID).

Patient management system 1400 generally includes one or more devices 1402, 1404, and 1406, one or more external interface devices 1408, a communication system 1410, one or more remote peripheral devices 1409, and a host 1412. The host 1412 may be a single computing device, such as a programmer or other patient management device. In some embodiments, the host 1412 is an external device that communicates directly with the one or more devices 1402, 1404, and 1406 and does not require the use of separate external interface devices 1408. In some embodiments, the host is an external device and receives data, such as EGM data, from an external database 1480.

Each component of the patient management system 1400 can communicate using the communication system 1410. Some components may also communicate directly with one another. The various components of the example patient management system 1400 illustrated herein are described below. The patient management system 1400 may be a single device or comprise multiple devices. In one embodiment, the patient management system 1400 is a single external computing device.

Data-generating devices 1402, 1404, and 1406 can be implantable devices or external devices that may provide one or more of the following functions with respect to a patient: (1) sensing, (2) data analysis, and (3) therapy. For example, in one embodiment, devices 1402, 1404, and 1406 are either implanted or external devices used to measure a variety of physiological, subjective, and environmental conditions of a patient using electrical, mechanical, and/or chemical means. In a variety of embodiments, at least one of the devices 1402, 1404, 1406 is an IMD.

The devices 1402, 1404, and 1406 can be configured to automatically gather data or can require manual intervention by the patient or another person. The devices 1402, 1404, and 1406 can be configured to store data related to the physiological and/or subjective measurements and/or transmit the data to the communication system 1410 using a variety of methods, described in detail below. Although three devices 1402, 1404, and 1406 are illustrated in the example embodiment shown, many more devices can be coupled to the patient management system. In one embodiment, each of the devices 1402, 1404 and 1406 is serving a different patient. In one embodiment, two or more devices are serving a single patient.

The devices 1402, 1404, and 1406 can be configured to analyze the measured data and act upon the analyzed data. For example, the devices 1402, 1404, and 1406 can be configured to modify therapy or provide an alarm based on the analysis of the data. As such, in a variety of embodiments, one or more of the devices 1402, 1404, 1406 can be components of the processing circuitry described above.

In one embodiment, devices 1402, 1404, and 1406 provide therapy. Therapy can be provided automatically or in response to an external communication. Devices 1402, 1404, and 1406 are programmable in that the characteristics of their sensing, therapy (e.g., duration and interval), or communication can be altered by communication between the devices 1402, 1404, and 1406 and other components of the patient management system 1400. Devices 1402, 1404, and 1406 can also perform self-checks or be interrogated by the communication system 1410 to verify that the devices are functioning properly. Examples of different embodiments of the devices 1402, 1404, and 1406 are provided herein.

Devices implanted within the body have the ability to sense and communicate as well as to provide therapy. Implantable devices can provide direct measurement of characteristics of the body, including, without limitation, electrical cardiac activity as described above, physical motion, temperature, heart rate, activity, blood pressure, breathing patterns, ejection fractions, blood viscosity, blood chemistry, blood glucose levels, and other patient-specific clinical physiological parameters, while minimizing the need for patient compliance. Derived measurements can also be determined from the implantable device sensors (e.g., a sleep sensor, functional capacity indicator, autonomic tone indicator, sleep quality indicator, cough indicator, anxiety indicator, and cardiovascular wellness indicator for calculating a quality of life indicator quantifying a patient's overall health and well-being).

Devices 1402, 1404, and 1406 can also be external devices, or devices that are not implanted in the human body, that are used to measure physiological data (e.g., a thermometer, sphygmomanometer, or external devices used to measure blood characteristics, body weight, physical strength, mental acuity, diet, heart characteristics, and relative geographic position).

The patient management system 1400 may also include one or more remote peripheral devices 1409 (e.g., cellular telephones, pagers, PDA devices, facsimiles, remote computers, printers, video and/or audio devices) that use wired or wireless technologies to communicate with the communication system 1410 and/or the host 1412.

The database module 1414 comprises memory for storing patient data. The patient data can include electrogram data, which comprises groups of device-identified beat locations for the electrogram data. This data may be received from a patient device, such as an implantable medical device, or it may be retrieved from another database 1480. The example database module 1414 includes a patient database 1440 and an episode database 1442, which are described further below. The patient database 1440 includes patient specific data, including data acquired by the devices 1402, 1404, and 1406, such as electrogram data, as well as a patient's medical records and historical information. The episode database 1442 has episode data regarding a plurality of different episodes generated from those of devices 1402, 1404, and 1406 that provide episode data. The episode database 1442 may also store data analyzed by the analysis module 1416.

Information can also be provided from an external source, such as external database 1480. For example, the external database 1480 could include external medical records maintained by a third party, such as drug prescription records maintained by a pharmacy, providing information regarding the type of drugs that have been prescribed for a patient or, in another example, authorization data from patient groups that have authorized users to view arrhythmia episode data. The external database 1480 may also store patient data that was previously acquired by an implantable or external medical device. One example of stored patient data on an external database 1480 is electrogram data.

The example analysis module 1416 includes a patient analysis module 1450 and a device analysis module 1452, which each can be referred to as components of the "processing circuitry" disclosed herein. Patient analysis module 1450 may utilize information collected by the patient management system 1400, as well as information for other relevant sources, to analyze data related to a patient and provide timely and predictive assessments of the patient's well-being. Device analysis module 1452 analyzes data from the devices 1402, 1404, and 1406 and external interface devices 1408 to predict and determine device issues or failures. For example, the device analysis module 1452 may analyze electrogram data to determine locations of heart beats on one or more channels. The device analysis module 1452 can further compare device-identified beats and beat locations to beats and beat locations determined using the multi-pass method. The device analysis module 1452 can then perform comparisons to find the presence of noise.

The analysis module 1416 further includes an adjudication processor 1458, and episode processor 1460 and an overwrite processor 1462, where each of the processors 1458, 1460, 1462 can be considered components of the "processing circuitry" disclosed herein. In one embodiment, the adjudication processor is operatively connected to at least the episode database 1442 and is configured to receive as input episode data regarding one of the different episodes.

The episode processor 1460 performs processing of the adjudication database in order to provide reports, patient alerts, or programming recommendations. The overwrite processor 1462 can analyze data provided from the episode database 1442, and other portions of the patient management system 1400 to determine what particular portion of episode data for one of the episodes from the episode database should be displayed to a user. Overwrite processor 1462 can, through the notification module 1418 described below, provide the means for graphically displaying a portion of data selected from arrhythmia episode data related to an episode of a patient, such as data generated by a data-generating device and stored in the episode database.

Overwrite processor 1462 also requests from a user any changes in the characterization data determined by the adjudication processor, and can articulate the request for user input characterizing an episode. The request may be a direct question to a user, a series of choices provided to the user, or simply a blank space on the user interface configured to accommodate the user input. The overwrite processor 1462 may also store the overwrite history for individual users.

One or more portions of the analysis module 1416, such as the adjudication processor 1458 and episode processor 1460 may be located remotely from other parts of the patient management system 1400. A microprocessor of a data-generating device may also serve as an adjudication processor in some embodiments.

Notification module 1418 coordinates the delivery of reports, patient alerts or programming recommendations based on the analysis performed by the host 1412. For example, based on the data collected from the devices and analyzed by the host 1412, the notification module 1418 can deliver information to the caregiver, user, or to the patient using, for example, a display provided on the external interface device 1408. A user interface device 1490 that is independent of a data-generating device may also be used to deliver information. The external interface device 1408 and user interface device 1490 are also configured, according to multiple embodiments, to display a report, alert, or programming recommendation, receive overwrite information from a user, and receive other data from the user. Displayed data, as described above, can be determined by the episode processor 1460, overwrite processor 1462 and notification module 1418.

External interface devices 1408 to display information, such as programmer/recorder/monitors, can include components common to many computing devices. User interface devices 1490 to display and received information from users can also include components common to many computing devices. Referring now to FIG. 10, a diagram of various components is shown in accordance with some embodiments of the invention. However, it is not required that an external interface device have all of the components illustrated in FIG. 10.

In one embodiment, the external interface device includes a central processing unit (CPU) 1505 or processor, which may include a conventional microprocessor, random access memory (RAM) 1510 for temporary storage of information, and read only memory (ROM) 1515 for permanent storage of information. A memory controller 1520 is provided for controlling system RAM 1510. A bus controller 1525 is provided for controlling data bus 1530, and an interrupt controller 1535 is used for receiving and processing various interrupt signals from the other system components.

Mass storage can be provided by diskette drive 1541, which is connected to bus 1530 by controller 1540, CD-ROM drive 1546, which is connected to bus 1530 by controller 1545, and hard disk drive 1551, which is connected to bus 1530 by controller 1550. User input to the programmer system may be provided by a number of devices. For example, a keyboard and mouse can be connected to bus 1530 by keyboard and mouse controller 1555. DMA controller 1560 is provided for performing direct memory access to system RAM 1510. A visual display is generated by a video controller 1565 or video output, which controls video display 1570. The external system can also include a telemetry interface 1590 or telemetry circuit which allows the external system to interface and exchange data with an implantable medical device. It will be appreciated that some embodiments may lack various elements illustrated in FIG. 10.

Figure 11:
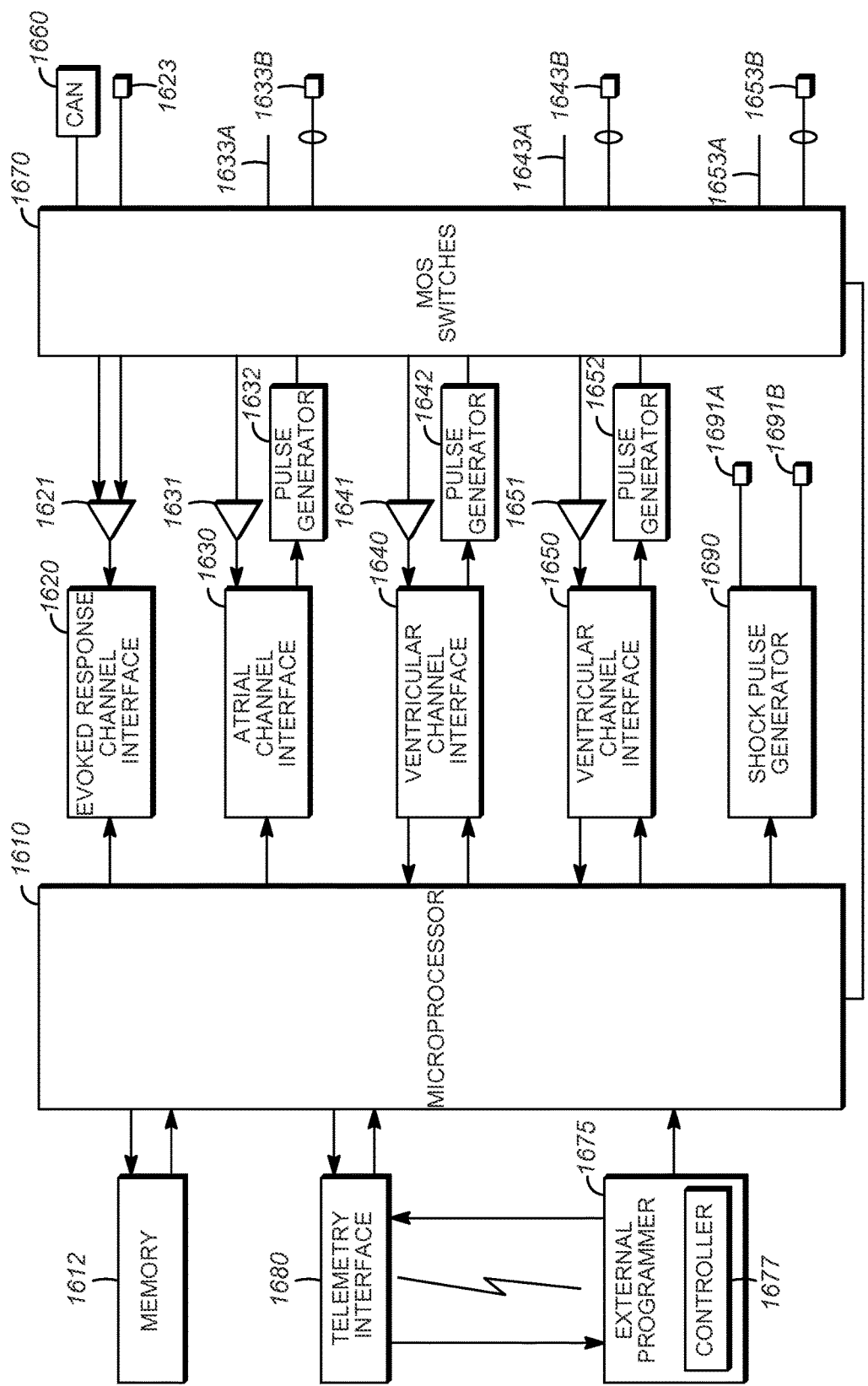
FIG. 11 depicts a schematic of some components of an exemplary implantable medical device.

Referring now to FIG. 11, some components of an exemplary IMD 1600 are schematically illustrated. The IMD 1600 can include a controller made up of a microprocessor 1610 communicating with a memory 1612, where the memory 1612 may comprise a ROM (read-only memory) for program storage and a RAM (random-access memory) for data storage. The controller could be implemented by other types of logic circuitry (e.g., discrete components or programmable logic arrays) using a state machine type of design, but a microprocessor-based system is preferable. The controller is capable of operating the IMD 1600 in a number of programmed modes where a programmed mode defines how pacing pulses are output in response to sensed events and expiration of time intervals.

A telemetry interface 1680 is provided for communicating with an external programmer 1675. The external programmer is a computerized device with a controller 1677 that can interrogate the IMD 1600 and receive stored data as well as adjust the operating parameters of the pacemaker.

The IMD 1600 has an atrial sensing/pacing channel comprising ring electrode 1633A tip electrode 1633B sense amplifier 1631, pulse generator 1632, and an atrial channel interface 1630 which communicates bi-directionally with a port of microprocessor 1610. The device also has two ventricular sensing/pacing channels that similarly include ring electrodes 1643A and 1653A tip electrodes 1643B and 1653B sense amplifiers 1641 and 1651, pulse generators 1642 and 1652, and ventricular channel interfaces 1640 and 1650. For each channel, the electrodes are connected to the IMD 1600 by a lead and used for both sensing and pacing. A MOS switching network 1670 controlled by the microprocessor is used to switch the electrodes from the input of a sense amplifier to the output of a pulse generator. A shock channel is also provided comprising a shock pulse generator 1690 and shock electrodes 1691A and 1691B that enables the device to deliver a defibrillation shock to the heart when fibrillation or other tachyarrhythmia is detected. The IMD 1600 also has an evoked response sensing channel that comprises an evoked response channel interface 1620 and a sense amplifier 1621 that has its differential inputs connected to a unipolar electrode 1623 and to the device housing or can 1660 through the switching network 1670. The evoked response sensing channel may be used to verify that a pacing pulse has achieved capture of the heart in a conventional manner or, as explained below, used to record an evoked response electrogram.

The channel interfaces include analog-to-digital converters for digitizing sensing signal inputs from the sensing amplifiers, registers that can be written to for adjusting the gain and threshold values of the sensing amplifiers, and, in the case of the ventricular and atrial channel interfaces, registers for controlling the output of pacing pulses and/or adjusting the pacing pulse energy by changing the pulse amplitude or pulse width. The microprocessor 1610 controls the overall operation of the device in accordance with programmed instructions stored in memory. The sensing circuitry of the IMD 1600 generates atrial and ventricular sense signals when voltages sensed by the electrodes exceed a specified threshold. The controller then interprets sense signals from the sensing channels and controls the delivery of paces in accordance with a programmed pacing mode. The sensed signals from any of the sensing channels of the IMD 1600 in FIG. 11 can be digitized and recorded by the controller to constitute an electrogram that can either be transmitted via the telemetry link 1680 to the external programmer 1675 or stored for later transmission. The patient's cardiac activity may thus be observed in real-time or over a selected historical period.

The above-described method can be regularly initiated to analyze the implanted leads. Gathered data may be used as input for other device functionality, such as arrhythmia adjudication.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as "arranged", "arranged and configured", "constructed and arranged", "constructed", "manufactured and arranged", and the like.

One of ordinary skill in the art will understand that the modules, circuitry, and methods shown and described herein with regard to various embodiments of the invention can be implemented using software, hardware, and combinations of software and hardware. As such, the illustrated and/or described modules and circuitry are intended to encompass software implementations, hardware implementations, and software and hardware implementations.

All publications and patent applications in this specification are indicative of the level of ordinary skill in the art to which this invention pertains. All publications and patent applications are herein incorporated by reference to the same extent as if each individual publication or patent application was specifically and individually indicated by reference.

This application is intended to cover adaptations or variations of the present subject matter. It is to be understood that the above description is intended to be illustrative, and not restrictive. The scope of the present subject matter should be determined with reference to the appended claims, along with the full scope of equivalents to which such claims are entitled.

We claim:

1. A method comprising:
   receiving, via a first lead portion and a sensor, implanted medical device data, sensed over a period of time of one day;
   applying, via a processor, first noise detection criteria to the medical device data sensed by the first lead portion;
   counting, via the processor, the number of detected noise events sensed by the first lead portion over the time period based on the first noise detection criteria;
   applying, via the processor, second noise detection criteria to the medical device data sensed by the sensor;
   counting, via the processor, the number of detected noise events over the sensor over the time period based on the second noise detection criteria;
   calculating, via the processor, the mean number of detected noise events over the time period, wherein at least the number of detected noise events sensed by the first lead portion and the number of detected noise events sensed by the sensor are included in the mean calculation;
   recording, via the processor, a determination of potential lead failure in the first lead if the number of detected noise events over the first lead over the time period is greater than the mean number of noise events by at least 5%; and
   displaying, on a user interface, an alert representing the determination of potential lead failure of the first lead.

2. The method of claim 1, further comprising recording a determination of potential electro-magnetic interference when the number of detected noise events over the first lead is within a margin of the mean number of noise events and the mean number of noise events is above a threshold.

3. The method of claim 1, wherein the first lead portion and the sensor are different locations along a single lead.

4. The method of claim 1, wherein the first lead portion and the sensor are different leads.

5. The method of claim 1, wherein the first noise detection criteria defines a first threshold number of beats that are faster than a first fast beat threshold and the second noise detection criteria defines a second threshold number of beats that are faster than second fast beat threshold, wherein the second fast beat threshold is different than the first fast beat threshold.

6. The method of claim 5, wherein the sensor is a right ventricular lead and the second fast beat threshold is 160 milliseconds.

7. The method of claim 5, wherein the sensor is a left ventricular lead and the second fast beat threshold is 275 milliseconds.

8. The method of claim 5, wherein the sensor is a right atrial lead and the second fast beat threshold is 110 milliseconds.

9. The method of claim 5, wherein the first threshold number of beats is four beats within an episode.

10. The method of claim 1, wherein the time period is at between 2 days and 30 days.

11. The method of claim 1, further comprising recording a determination representing potential lead failure in the sensor if the number of detected noise events over the sensor over the time period is greater than the mean number of noise events.

12. A system comprising:
an implantable medical device having a plurality of sensors configured to sense patient physiological data, wherein the plurality of sensors comprise at least one lead;
processing circuitry configured to:
receive the patient physiological data from the plurality of sensors over a period of time of one day,
apply noise detection criteria to patient physiological data sensed by each of the plurality sensors to count the number of noise events over each sensor,
calculate the mean number of noise events from all of the sensors over the period of time, and
compare the number of noise events from each of the at least one lead to the mean number of noise events over the period of time; and
a user interface in communication with the processing circuitry configured to display an alert representing potential lead failure for each of the at least one lead that had a total number of noise events greater than the mean number of noise events over the period of time.

13. The system of claim 12, wherein the processing circuitry is disposed within the implantable medical device.

14. The system of claim 12, wherein a portion of the processing circuitry is disposed within the implantable medical device and another portion of the processing circuitry is disposed in a communicator that is configured for communication with the implantable medical device.

15. The system of claim 12, wherein the processing circuitry is configured to apply different noise detection criteria to each of the sensors.

16. The system of claim 12, wherein the processing circuitry is configured to receive the patient physiological data that was sensed over a time period between 2 days and 30 days.

17. The system of claim 12, wherein the user interface is configured to display an alert of potential electro-magnetic interference when the number of detected noise events over the at least one lead is within a margin of the mean number of noise events and the mean number of noise events is above a threshold.

18. The system of claim 15, wherein the at least one lead comprises a first lead that is a right atrial lead and the processing circuitry is configured to apply a first noise detection criteria to the first lead that comprises sensing a plurality of sensed beats within an episode that are faster than 110 milliseconds.

19. The system of claim 18, wherein the at least one lead comprises a second lead that is a left ventricular lead and the processing circuitry is configured to apply a second noise detection criteria to the second sensor that comprises sensing a plurality of sensed beats within an episode that are faster than 275 milliseconds.

20. The system of claim 12, wherein the noise detection criteria requires at least four beats within an episode to be faster than a threshold.

* * * * *